US007643869B1

(12) United States Patent
Dabiri et al.

(10) Patent No.: US 7,643,869 B1
(45) Date of Patent: Jan. 5, 2010

(54) APPARATUS FOR NON-INVASIVE CANCEROUS TISSUE DIAGNOSIS AND TOMOGRAPHY USING TERAHERTZ IMAGING

(76) Inventors: Ali E. Dabiri, 2290 Middleton Way, San Diego, CA (US) 92109; Manoucher E. Motamedi, 756 Paseo De leon, Newbury Park, CA (US) 91320

( * ) Notice: Subject to any disclaimer, the term of this patent is extended or adjusted under 35 U.S.C. 154(b) by 1332 days.

(21) Appl. No.: 10/801,922

(22) Filed: Mar. 17, 2004

(51) Int. Cl.
*A61B 6/00* (2006.01)
(52) U.S. Cl. .................. 600/476; 359/569; 359/571
(58) Field of Classification Search .......... 600/407, 600/473, 476, 478; 359/577
See application file for complete search history.

(56) References Cited

U.S. PATENT DOCUMENTS

| 4,170,987 | A |  | 10/1979 | Anselmo et al. |
|---|---|---|---|---|
| 4,515,165 | A |  | 5/1985 | Carrol |
| 4,556,057 | A |  | 12/1985 | Hiruma et al. |
| 4,948,974 | A |  | 8/1990 | Nelson et al. |
| 5,040,889 | A | * | 8/1991 | Keane .................. 356/51 |
| 5,172,685 | A |  | 12/1992 | Nudelman |
| 5,318,024 | A |  | 6/1994 | Kittrell et al. |
| 5,507,287 | A |  | 4/1996 | Palcic et al. |
| 5,730,147 | A | * | 3/1998 | Craig .................. 600/549 |
| 5,782,770 | A |  | 7/1998 | Mooradian et al. |
| 6,078,047 | A |  | 6/2000 | Mittleman et al. |
| 6,992,824 | B1 |  | 1/2006 | Motamedi et al. |
| 2001/0043163 | A1 | * | 11/2001 | Waldern et al. ............ 345/7 |
| 2003/0149346 | A1 | * | 8/2003 | Arnone et al. ........... 600/309 |
| 2004/0155665 | A1 | * | 8/2004 | Arnone et al. ........... 324/644 |
| 2004/0254435 | A1 | * | 12/2004 | Mathews et al. .......... 600/372 |
| 2005/0143754 | A1 | * | 6/2005 | Zelickson et al. ........ 606/131 |

OTHER PUBLICATIONS

M.E. Motamedi, et al, "MOEM Scan Engine for Barcode Reading and Factory Automation," SPIE Proceeding of Miniaturized Systems with Microoptics and Micromechanics III, vol. 3276, pp. 66-80 San Jose, 1998.
Mahadevan-Jansen A., et al., Development of a Fiber Optic Probe to measure Raman Spectra of Spectra of Cervical Tissue in vivo, Photochemistry and Photobiology, 68(3), 427-431,1998.
Ramanujam N., et al., Spectroscopic Diagnosis of Cervical Intraepithelial Neoplasia(CIN) in Vivo using Laser—Induced Fluorescence Spectra at Multiple Excitation Wavelengths, Laser Surgery and Medicine, 19(1), 63-74,1996.
Ramanujam N., et al., "Fluorescence Spectroscopy: A diagnostic Tool for Cer Intraepithelial Neoplasia (CIN), "Gynecologic Oncology, 52, 31-38, 1994.

* cited by examiner

*Primary Examiner*—Brian Casler
*Assistant Examiner*—Jonathan G Cwern

(57) ABSTRACT

The primary objective of the present method and apparatus is to provide a portable and new diagnosis system for quickly and reliably examining tissue conditions. The method uses the most advance miniaturized micro-opto-electro-mechanical systems (MOEMS) system for generating a rapid variable optical delay line capable of generating wideband terahertz pulses. The method detects and analyzes cancerous tissues by comparing a plurality of spectrum resolved images of suspected tissue without applying harmful agents into the tissue to facilitate interaction with illumination sources. The method employs non-evasive, real time terahertz imaging systems and techniques to diagnose tissue for detecting the presence of cancer. A map showing, which tissue is healthy and which is cancerous can aid in the accurate removal of cancerous tissue.

7 Claims, 4 Drawing Sheets

(a)

(b)

(c)

APPARATUS FOR NON-INVASIVE CANCEROUS TISSUE DIAGNOSIS AND TOMOGRAPHY USING TERAHERTZ IMAGING

FIELD OF THE DISCLOSED METHOD AND APPARATUS

This method and apparatus is related to non-invasively diagnosing cancerous tissue, using terahertz systems and more specifically to tomography of the tissue using terahertz imaging.

BACKGROUND

The tissue diagnosis of cancer is routinely performed by standard surgical histo-pathological analysis, which involves preparation of tissue and then viewing under the microscope. This method is painful for patients, time consuming, and its results can take up to a few days to be ready. Direct visualization is also used, but is weakened by subjective decision. Currently, a frozen section diagnostic method is employed for operating room situations, where there is a need for immediate results. This technique can take up to 30 minutes. There are major difficulties with this method, primarily due to inaccurate diagnosis and a large amount of artifact in the tissue preparation. One of the most difficult issues involves finding a location having an appropriate surgical margin.

A number of systems have been developed in the past twenty years to perform biopsy on tissue by optical techniques. The early nineteen-eighties saw the development of simple systems which would irradiate either UV, visible, or infrared lights onto the tissue, and attempt to characterize the resulting reflectance or fluorescence emission spectra. This type of illumination was not always specific. Furthermore, high levels of tissue autofluorescence were observed. Therefore, there was a need to develop specific tumor markers such as Homoproto Porphorin Derivative (HPD). These substances were accordingly developed. HPDs are injected into tissue before laser illumination. After a suitable time, laser interrogation is performed. Problems of toxicity, patient safety, and convenience have prevented the widespread use of these photodynamic agents.

Later attempts to use laser induced fluorescence as a diagnostic tool resulted in the development of simple single fiber systems. Such systems illuminate the suspect areas of tissue with laser light at a focal point where a single fiber relays the tissue fluorescence. Actual spectral differences were found to exist between normal tissue and abnormal tissue. These studies have led to an array of spectral analysis technique, but they have all been limited to three or four spectral lines corresponding to reflectance of fluorescence signature peaks. The exact reason for the differences in normal versus cancerous tissue are not understood, but might be related to the three-dimensional structure or differences in biochemical makeup. The ability to exploit these differences can be used as a diagnostic tool.

Although these systems are relatively simple to use and can be adapted to existing endoscopic and colonoscopic instruments for measurements, they have three fundamental limitations:

1. The techniques can easily miss a small tumor since single fiber illumination area is extremely small.
2. The techniques cannot provide information on surgical margins during operative procedure due to lack of imaging capabilities.
3. Most techniques require the application of photodynamic agents.

Mooradian et al., in U.S. Pat. No. 5,782,770 have proposed a technique for diagnosing tissue via hyperspectral imaging. In this technique, the spectral content of the image can be analyzed on a pixel-by-pixel basis to determine the presence of certain matter. Although this technique operates in real time and is non-invasive, it provides information only from the surface of the tissue. A real time three-dimensional tomography is needed to fully differentiate normal tissue from abnormal tissue.

Accordingly, a real time, non-invasive method is needed to rapidly diagnose the tissue, reduce the uncertainty of tissue diagnosis, and provide an actual image to identify the exact surgical margins during operative procedures.

BRIEF SUMMARY OF THE DISCLOSED METHOD AND APPARATUS

The primary objective of the present method and apparatus is to provide new systems and methods for the diagnosis of tissue conditions. It is also the objective of the present method and apparatus to provide systems and methods for detecting and analyzing cancerous tissues by comparing a plurality of spectrum resolved images of suspected tissue.

The present method and apparatus employs non-evasive, real time terahertz imaging systems and techniques to diagnose tissue for detecting the presence of cancer. The present method and apparatus can be distinguished from similar techniques in that a terahertz image contains detailed spectral information which can be analyzed for spectral signature characteristics not found in auto-fluorescence and similar emission mechanisms.

Terahertz waves are a segment of electromagnetic waves. Terahertz waves are bounded between millimeter waves (less than $1 \times 10^{11}$ Hz) and photonics waves (greater than $1 \times 10^{13}$). The electromagnetic frequencies lower than terahertz band are covering mm waves (microwaves), while the electromagnetic frequencies higher than terahertz band are covering near infrared through visible spectrum.

Terahertz wave band can be used for time domain and frequency domain imaging. The present applications of terahertz are spectroscopy in atmospheric science and in astronomy, imaging for burn diagnostics, tomography, biomedical, medical diagnostics, screening for weapon, explosives, biohazard, and finally imaging of concealed objects.

Existing water in living tissue limits the penetration depth of terahertz energy to a few millimeters, which is just sufficient for the diagnosis of cervical cancer. Terahertz waves above 0.5 THz can travel in air up to a meter, which is more than sufficient to transmit and receive signals from a cervix.

Besides detecting the presence of cancer, the present method and apparatus is also valuable to locate the extent of the spread of cancerous tissue as well as the progression of the cancer. A map showing, which tissue is healthy and which is cancerous, can aid in the accurate removal of cancerous tissue. However, systems employing single point detection do not show the extent of the affected tissue region. But when using terahertz systems such as disclosed herein, the combination of the spatial resolution and the high spectral resolution of a terahertz imaging system can be utilized to detect cancerous tissues.

The present method and apparatus does not require introduction of harmful agents into the tissue.

The present method and apparatus gathers data in three spatial dimensions. Initially, a spot is selected on the tissue and a line image is constructed through the depth of the tissue.

The depth of the tissue is binned according to the desired spatial resolution and signal-to-noise ratio. Then, the incident beam will be scanned in a horizontal direction alongside of the tissue. Successive line images along the depth of the tissue will be collected. Finally, the beam will be scanned in the orthogonal direction to start a new horizontal scan. The same information will be gathered successively over the entire tissue. A tomography will then be constructed from the gathered overall data.

A better understanding could be achieved with reference to Detailed Description of the disclosed method and apparatus and with reference to the drawings. The description represents a particular case to realize the disclosed method and apparatus and is not intended to define the invention, but merely to provide adequate support for the claims appended hereto. Accordingly, the invention is defined solely by the claims to the invention appended hereto.

DETAILED DESCRIPTION

Figure 1:
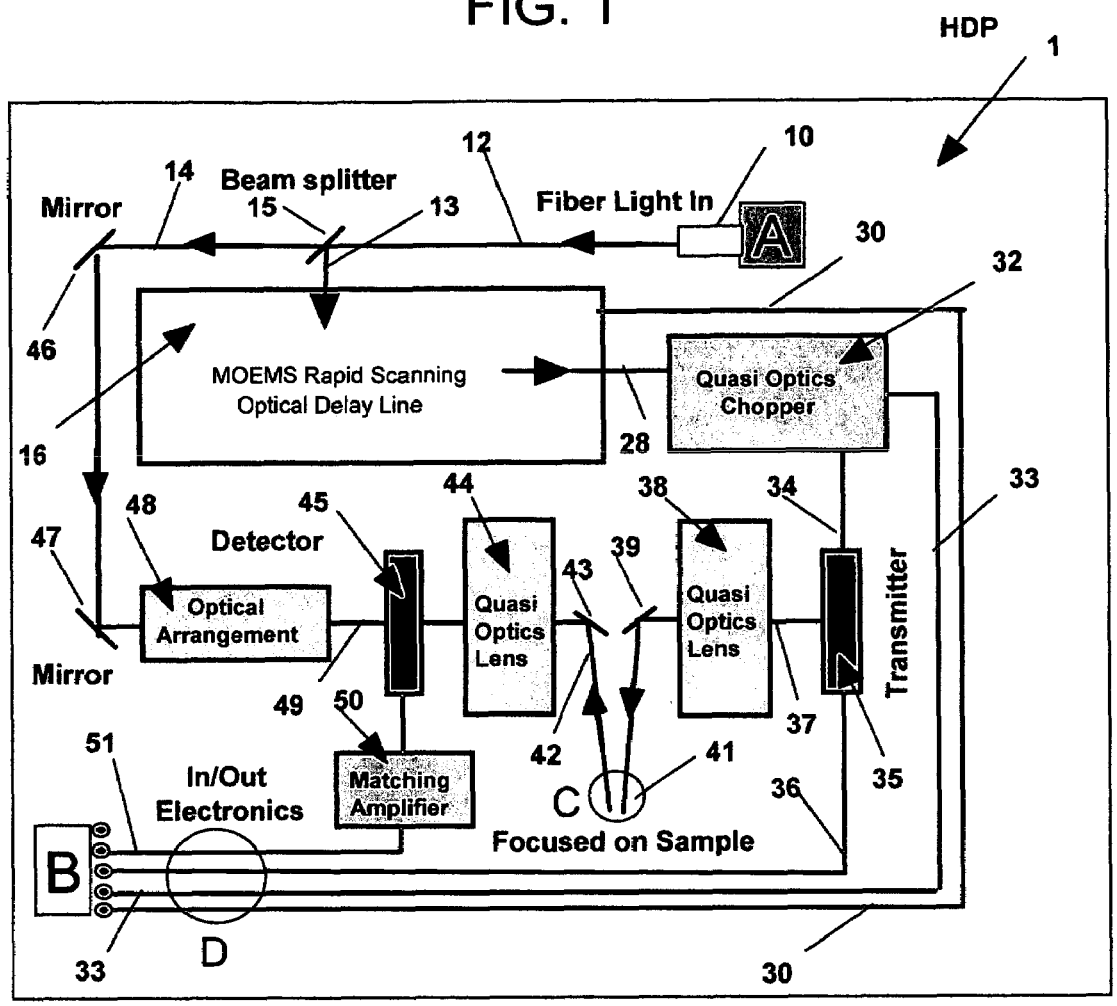
FIG. 1 is a simplified block diagram of the diagnostic probe of the present invention.
Figure 2:
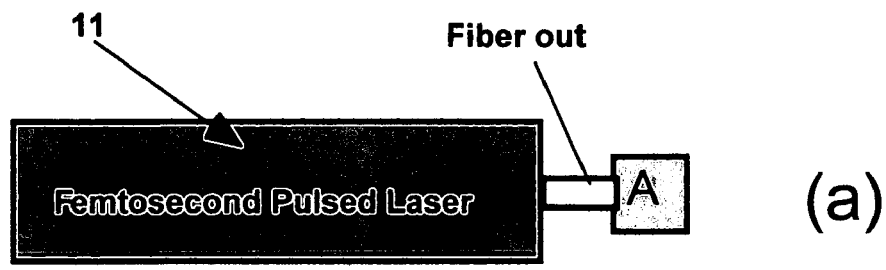
FIGS. 2a-c are the simplified block diagrams of the system components outside of the diagnostic probe.
Figure 2:
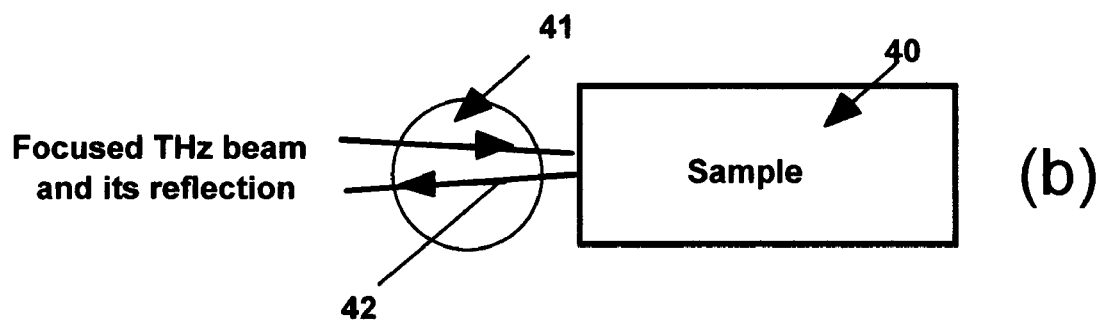
Figure 2:
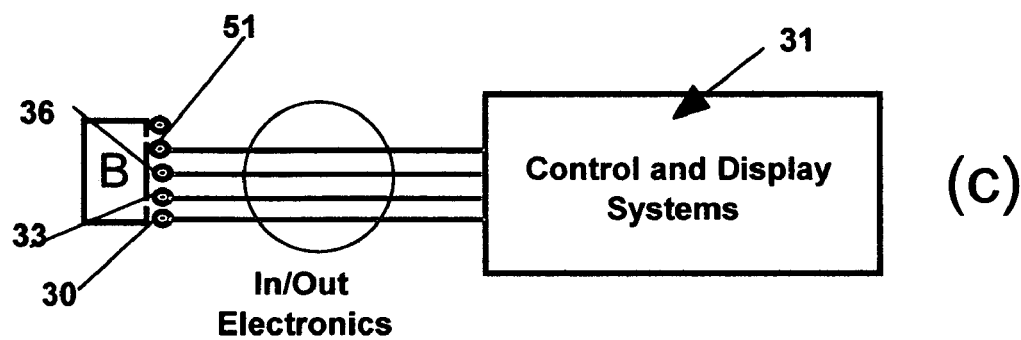

As shown in FIG. 1, a fiber carrier laser light 10, in accordance with the present method and apparatus is generated by a femtosecond pulsed laser 11 shown in FIG. 2a with wavelength typically between 800 nanometers to 1.5 μm. The laser light is gated by time domain pulses, the durations of which are preferably measured in femtoseconds. The frequency spectrum of a femtosecond pulse is rather wide, covering from 300 GHz to 10 THz (10,000 GHz). The output beam of the pulsed laser 11 is coupled to the fiber carrier laser light 10 shown in FIG. 1, thus transferring the femtosecond pulses to a handheld diagnostic probe (HDP) 1. All components contained in HDP 1 are shown in FIG. 1. All components required for HDP 1 operation that lie outside the HDP 1 are shown in FIGS. 2a, 2b, and 2c. The laser light 12 inside the HDP will split into a pump light 13 and a reference (probe) light 14 by a beam splitter 15.

Figure 3:
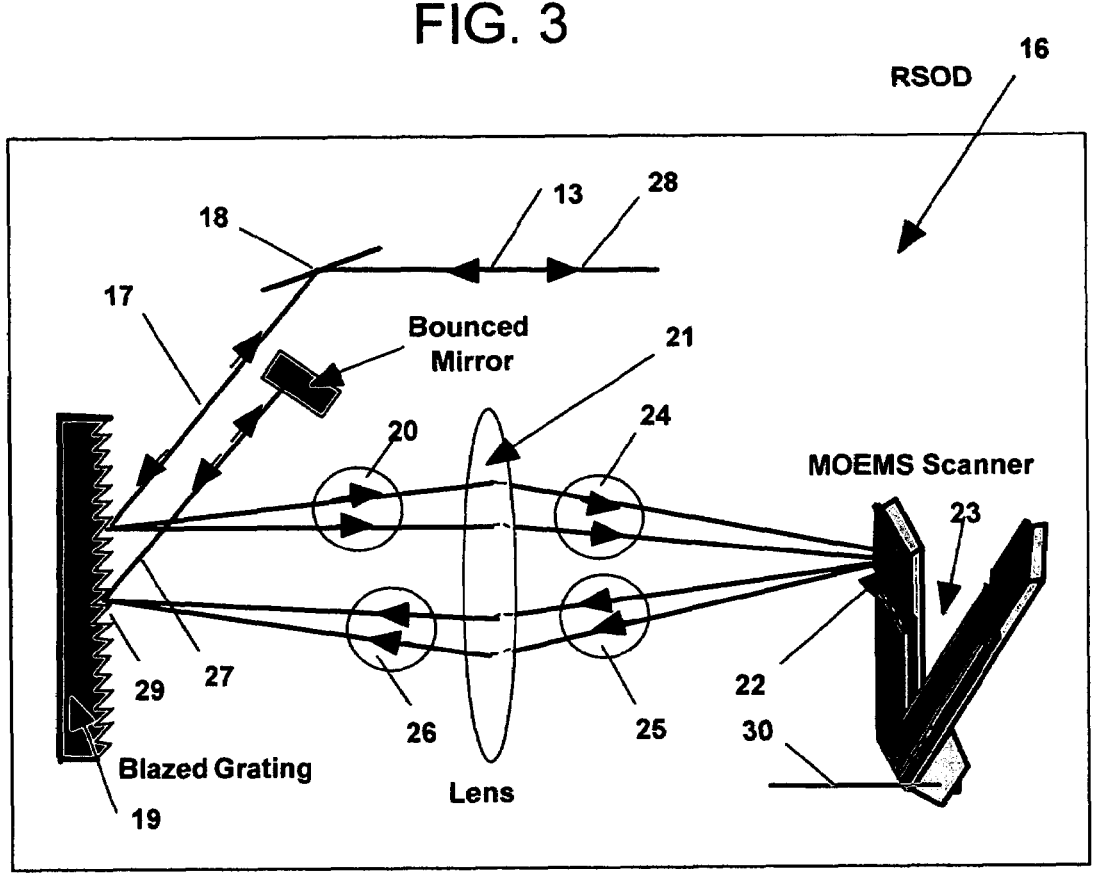
FIG. 3 is a simplified block diagram of the MOEMS rapid scanning optical delay line.

The pump light 13 will enter a micro-opto-electro-mechanical systems (MOEMS) rapid scanning optical delay line (RSOD) 16. The detail description of the MOEMS RSOD 16 is provided in a U.S. Pat. No. 6,839,172 entitled "Enhanced sampling rate in time domain imaging using MOEMS scanning optical delay line" and its components are shown in FIG. 3. As shown in FIG. 3, pump beam 13 will reflect beam light 17 by mirror 18 to a special design blazed grating 19. Beam 17 will split in zero and +1 diffraction order beams 20. The beams 20 focus through a lens 21 on a MOEMS scanner mirror 22. MOEMS scanner 23 has potential to have large-size mirrors (more than 10 mm²) and a surface flatness on the order of optical wavelength, as described in an article entitled "MOEM Scan Engine for Barcode Reading and Factory Automation" by M. E. Motamedi, et al published in SPIE Proceeding Of Miniaturized Systems with Micro-optics and Micromehanics III, Vol., 3276, p.p. 66-80, 1998. The reflection beam 25 from scanner mirror 22 is setup to pass through the same lens 21 and refocus again to beams 26 arriving at a new location on grating 19, combining to single beam. A bouncing mirror is mounted in proper location which returns the light beam 27 back through lens 21 and scanner mirror 22 and redirects the beam back from beam 17 and mirror 18 to the direction of beam 13. As the scanner mirror 22 relocates to a new location, the return beams 26 will move on the surface of the grating 19 from location 29 to another scanned location generating time delays of tens of picoseconds. The power required for operating the MOEMS RSOD 16 is fed through the HDP 1 connector 30 from control and display system 31.

The return scanning delayed beam 24 is output through beam light 28 from the RSOD line to a quasi-optics chopper 32. The input power and the returned chopping signals are coupled from the quasi optics chopper 32 to the control and display system 31 through connector 33. The chopped beam output 34 exits from the quasi optics chopper system 32 and enters a terahertz transmitter system 35. The transmitter system 35 is a preferably a solid state, semi-insulated GaAs, electromagnetic emitter coupled by metal-film strip lines about 10 μm wide and spaced 100 μm apart. For the purpose of this description, the transmission lines are considered to be part of the transmitter system 35. As the number of the lines increases, the emitter bandwidth decreases. If the transmitter is excited by a train of femtosecond pulses emitted from the beam quasi optics chopper 32, the strip lines in the transmitter system 35 act as an antenna and radiate waves in the terahertz spectrum. If only two strips are used, the system 35 radiates in a spectrum ranging from 100 GHz to sometimes 10 THz. In the presently disclosed method and apparatus, the particular range of terahertz frequencies will be selected in accordance with what is demanded by type of diagnostic or other application. The transmitter system 35 requires a DC voltage for biasing, which is provided through the connector 36 from the system 31 shown in FIG. 2c.

Figure 4:
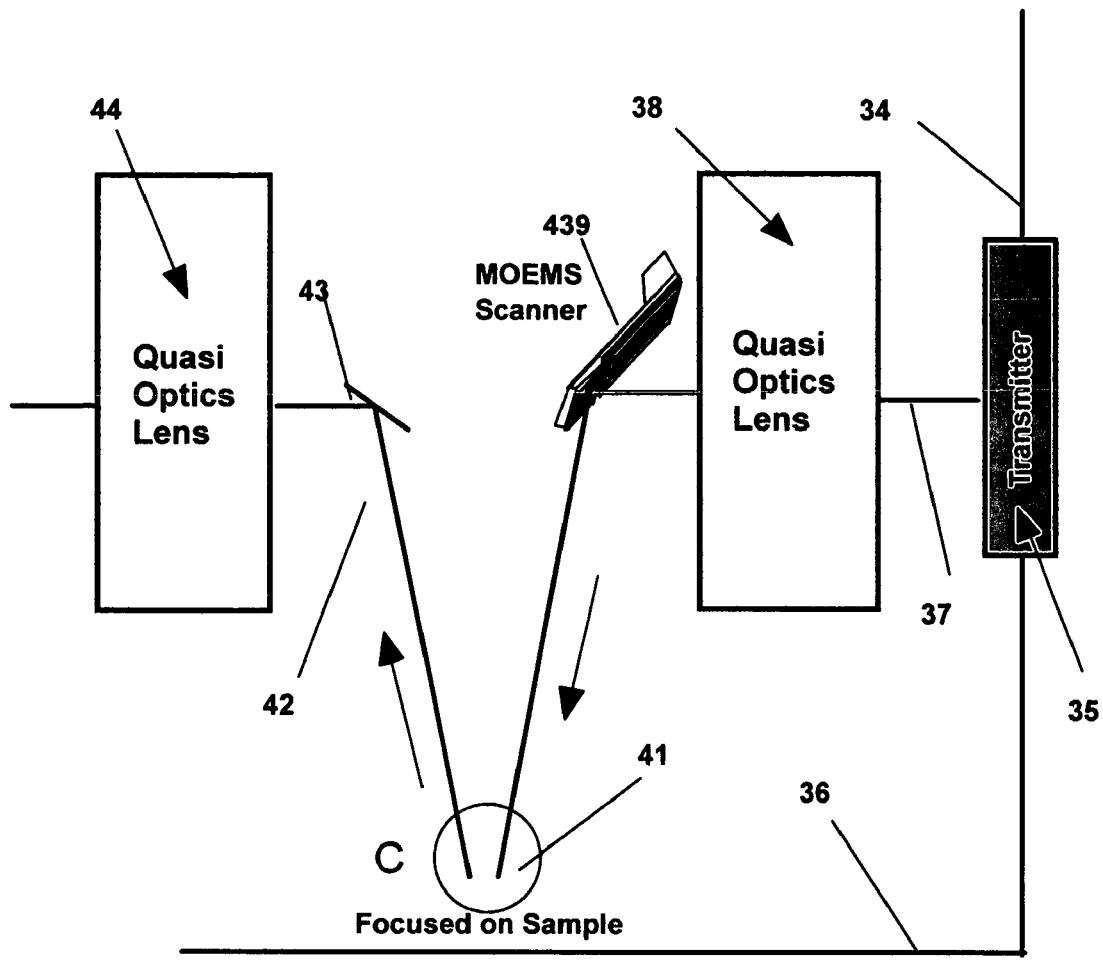
FIG. 4 is a portion of FIG. 1 where projection mirror is replaced by a MOEMS scanner.

The terahertz waves 37 emitted from the transmitter system 35 are focused through a quasi optics lens 38 and a mirror 39 to the tissue sample 40 shown in FIG. 2b. The sample 40, which is outside the probe, is diagnosed by a projection beam 41 (shown in both FIG. 1 and FIG. 2b) and its reflection beam. The focusing spot and its propagation through the tissue, taking into consideration the diffusion and dispersion phenomenon, are controlled by quasi optics lens 38 shown in FIG. 1. To cover a large area of tissue, the patient's tissue should be translated in well-defined position steps by a precision mechanical sample stepper. In some sophisticated models of the presently disclosed method and apparatus, the beam can be scanned inside the probe by a MOEM scanner 439. This option is shown in FIG. 4. The stepper power and control systems are supplied by the control and display system 31.

The reflection 42 from patient tissue sample is collected by the mirror 43 and is focused by quasi optics lens 44 onto a detector 45. The detector 45 preferably has the same structure and principles as discussed for the transmitter system 35. The received signal at the detector 45 has an inherently high signal to noise ratio, but it suffers significantly from misalignment and large bandwidth requirements. The detection process works based on convolution of two electromagnetic waves coming in opposite direction and mixed. Since the mixed waves are identical in characteristic when split at beam splitter 15, the detector acts as a convolver where the difference signal has the frequency of stepper with diagnosis information of the tissue under test.

The probe beam 14, which is split from beam splitter 15, enters in optical arrangement 48 via mirrors 46 and 47. A controlled terahertz reference beam 49 exits from the optical arrangement 48 and enters the detector 45 at the exact time arrival as the reflected terahertz signal 42 carrying information regarding the patient tissue sample. The mixing of these two terahertz waves within the detector 45 will detect the sample information. The detected output has high input impedance. The output preferably goes through several improvement stages, including a matching impedance amplifier 50. Using a MOEMS high speed scanning delay line allows the layer information of the tissue to be collected. In addition, a representative tomography of the tissue volume is constructed.

The sample information of the detector 45 is transferred in real time in the display and control system 31. The detector 45 is coupled to the display and control system 31 through the connector 51. The diagnosis results can then be displayed in a handheld display system. Alternatively, the diagnosis results could be transmitted to a medical center by means such as wireless communications.

The tissue image is comprised of a plurality of horizontal bands, each band being adjacent to another, with equal bandwidths and comprised of a plurality of pixels where each pixel being adjacent to another. The images with a calibrated reference are stored in a handheld memory, indicating regions of coincidence and region of non-coincidence, and combining the images at different layers to obtain the tomography of the tissue It should be understood by those skilled in the art that modifications from the disclosed method and apparatus may be made without departing from the spirit of the invention claimed in the appended claims provided herein. Furthermore, the invention is defined only by the appended claims. Accordingly, it will be understood that the above description is provided only to enable one of ordinary skill in the art to make and use the invention. However, departures from the disclosed method and apparatus that fall within the scope of the claims should be considered to be within the scope of the claimed invention.

We claim:

1. A handheld apparatus for diagnosis of tissue, comprising:
   a housing, the housing further comprising:
   a) a light source;
   b) a micro-opto-electro-mechanical systems (MOEMS) rapid scanning delay line coupled to the light source;
   c) a quasi optics chopper coupled to the MOEMS rapid scanning delay line;
   d) a terahertz transmitter coupled to the quasi optics chopper;
   e) a first quasi optics system coupled to the transmitter, the first quasi optics system outputting light directed at a tissue sample;
   f) a second quasi optics system adapted to be optically coupled to the tissue sample, the second quasi optics system receiving light reflected from the tissue sample;
   g) a detector coupled to the second quasi optic system;
   h) a matching amplifier coupled to the detector;
   i) a sample stepper; and
   j) a control and display system coupled to the sample stepper, the matching amplifier, the transmitter, the quasi chopper and the scanner.

2. The apparatus of claim 1, wherein a femtosecond pulsed laser is transmitted through a fiber for the handheld apparatus.

3. The apparatus of claim 1, wherein the MOEMS rapid scanning delay line is a miniature package.

4. The apparatus of claim 1, wherein the sample stepper is outside the housing.

5. The apparatus of claim 1, wherein a display system is inside the housing.

6. The apparatus of claim 1, wherein a display system is outside the housing.

7. The apparatus of claim 1, wherein quasi optics kinoform lenses are used for size reduction suitable for a handheld diagnosis system.

* * * * *